(12) United States Patent
Couture

(10) Patent No.: US 11,684,426 B2
(45) Date of Patent: Jun. 27, 2023

(54) SYSTEM AND METHOD FOR TRACKING BONES

(71) Applicant: ORTHOSOFT INC., Montreal (CA)

(72) Inventor: Pierre Couture, Montreal (CA)

(73) Assignee: ORTHOSOFT ULC, Montréal (CA)

( * ) Notice: Subject to any disclaimer, the term of this patent is extended or adjusted under 35 U.S.C. 154(b) by 287 days.

(21) Appl. No.: 16/556,837

(22) Filed: Aug. 30, 2019

(65) Prior Publication Data

US 2020/0069375 A1    Mar. 5, 2020

Related U.S. Application Data

(60) Provisional application No. 62/725,639, filed on Aug. 31, 2018.

(51) Int. Cl.
*A61B 34/20* (2016.01)
*A61B 34/10* (2016.01)
*A61B 90/00* (2016.01)

(52) U.S. Cl.
CPC .............. *A61B 34/20* (2016.02); *A61B 34/10* (2016.02); *A61B 90/39* (2016.02);
(Continued)

(58) Field of Classification Search
CPC ......... A61B 34/20; A61B 34/10; A61B 90/39; A61B 2034/2048; A61B 2034/2065; A61B 2034/107; A61B 2090/3983; A61B 2034/2055; A61B 2034/2068; A61B 2034/2051; A61B 2034/2063; A61B 2090/3991; A61B 2034/2059; A61B 34/40

See application file for complete search history.

(56) References Cited

U.S. PATENT DOCUMENTS

| 1,941,468 A | 1/1934 | Gilbert |
| 3,895,525 A | 7/1975 | Eichelberger et al. |

(Continued)

FOREIGN PATENT DOCUMENTS

| CA | 3053904 A1 * | 2/2020 | ............ A61B 34/20 |
| DE | 4231101 | 3/1994 | |

(Continued)

*Primary Examiner* — Boniface Ngathi N
*Assistant Examiner* — Zainab Mohammed Aldarraji
(74) *Attorney, Agent, or Firm* — Norton Rose Fulbright Canada LLP

(57) ABSTRACT

A system for determining a position and an orientation of a bone of an anatomical feature includes a trackable reference device having a surgical pin at a first position being attachable to the bone. A wearable attachment attached to the trackable reference device is configured to be mounted about the outer-skin surface of the anatomical feature. A distance sensor mounted to the trackable reference device at a second position is operable to determine a distance measurement of the second position of the trackable reference device from the bone. Reference markers are fixedly mounted to the trackable reference device. A position sensing device registers position and orientation readings of the reference markers in a reference coordinate system. A processing unit determines the position and the orientation of the bone in the reference coordinate system using the position and orientation readings and the distance measurement.

20 Claims, 4 Drawing Sheets

(52) U.S. Cl.
CPC . *A61B 2034/107* (2016.02); *A61B 2034/2048* (2016.02); *A61B 2034/2055* (2016.02); *A61B 2034/2065* (2016.02); *A61B 2034/2068* (2016.02); *A61B 2090/3983* (2016.02)

(56) References Cited

U.S. PATENT DOCUMENTS

| | | | |
|---|---|---|---|
| 4,305,296 | A | 12/1981 | Green et al. |
| 5,197,476 | A | 3/1993 | Nowacki et al. |
| 5,249,581 | A | 10/1993 | Horbal et al. |
| 6,106,463 | A | 8/2000 | Wilk |
| 6,159,152 | A | 12/2000 | Sumanaweera et al. |
| 6,190,320 | B1 | 2/2001 | Lelong |
| 6,213,958 | B1 | 4/2001 | Winder |
| 6,314,310 | B1 | 11/2001 | Ben-Haim et al. |
| 6,390,982 | B1 | 6/2002 | Bova et al. |
| 6,514,219 | B1 | 2/2003 | Guimond et al. |
| 6,529,758 | B2 | 3/2003 | Shahidi |
| 6,585,651 | B2 | 7/2003 | Nolte et al. |
| 6,585,731 | B1 | 7/2003 | Rattner et al. |
| 6,702,746 | B1 | 3/2004 | Srouji |
| 6,725,082 | B2 | 4/2004 | Sati et al. |
| 6,746,402 | B2 | 6/2004 | Ustuner |
| 6,768,496 | B2 | 7/2004 | Bieger et al. |
| 7,938,777 | B2 * | 5/2011 | Amiot ............... A61B 34/20 600/437 |
| 8,357,165 | B2 * | 1/2013 | Grant ............... A61B 90/39 606/86 R |
| 10,835,319 | B2 * | 11/2020 | Falardeau ............ A61B 34/10 |
| 11,103,315 | B2 * | 8/2021 | Malackowski ...... A61B 90/361 |
| 2002/0065461 | A1 | 5/2002 | Cosman |
| 2002/0087101 | A1 | 7/2002 | Barrick et al. |
| 2002/0120192 | A1 | 8/2002 | Nolte et al. |
| 2003/0018255 | A1 | 1/2003 | Martin et al. |
| 2003/0036762 | A1 | 2/2003 | Kerr et al. |
| 2004/0068260 | A1 | 4/2004 | Cossette et al. |
| 2004/0147839 | A1 | 7/2004 | Moctezuma |
| 2004/0230199 | A1 | 11/2004 | Jansen et al. |
| 2005/0015022 | A1 | 1/2005 | Richard et al. |
| 2005/0085720 | A1 | 4/2005 | Jascob et al. |
| 2005/0085822 | A1 | 4/2005 | Thornberry et al. |
| 2005/0101866 | A1 | 5/2005 | Goodwin |
| 2005/0143676 | A1 | 6/2005 | De Guise et al. |
| 2005/0238216 | A1 | 10/2005 | Yoden |
| 2007/0073121 | A1 | 3/2007 | Hoarau et al. |
| 2007/0100325 | A1 | 5/2007 | Jutras et al. |
| 2007/0225595 | A1 * | 9/2007 | Malackowski ........ A61B 34/20 600/424 |
| 2008/0021309 | A1 * | 1/2008 | Amiot ................... A61B 90/39 600/425 |
| 2008/0021310 | A1 * | 1/2008 | Amiot ................... A61B 34/20 600/425 |

FOREIGN PATENT DOCUMENTS

| | | | | |
|---|---|---|---|---|
| DE | 10136737 | | 2/2003 | |
| DE | 10346615 | | 5/2005 | |
| EP | 0353209 | | 1/1990 | |
| EP | 1161194 | | 12/2001 | |
| EP | 0966691 | | 8/2005 | |
| EP | 1935365 | A1 * | 6/2008 | ............. A61B 90/39 |
| EP | 2611379 | B1 * | 12/2017 | ............. A61B 90/36 |
| JP | 2005160704 | | 6/2005 | |
| WO | 2004/014488 | | 3/2000 | |
| WO | 2005/039391 | | 7/2000 | |
| WO | 2005/043319 | | 7/2000 | |
| WO | 0164094 | | 9/2001 | |
| WO | 0224075 | | 3/2002 | |
| WO | 0224094 | | 3/2002 | |
| WO | 03009772 | | 2/2003 | |
| WO | 2004/016178 | | 2/2004 | |
| WO | 2004/030559 | | 4/2004 | |
| WO | 2004/069073 | | 8/2004 | |
| WO | 2005/092198 | | 10/2005 | |
| WO | 2006/079211 | | 8/2006 | |
| WO | 2006/128301 | | 12/2006 | |

* cited by examiner

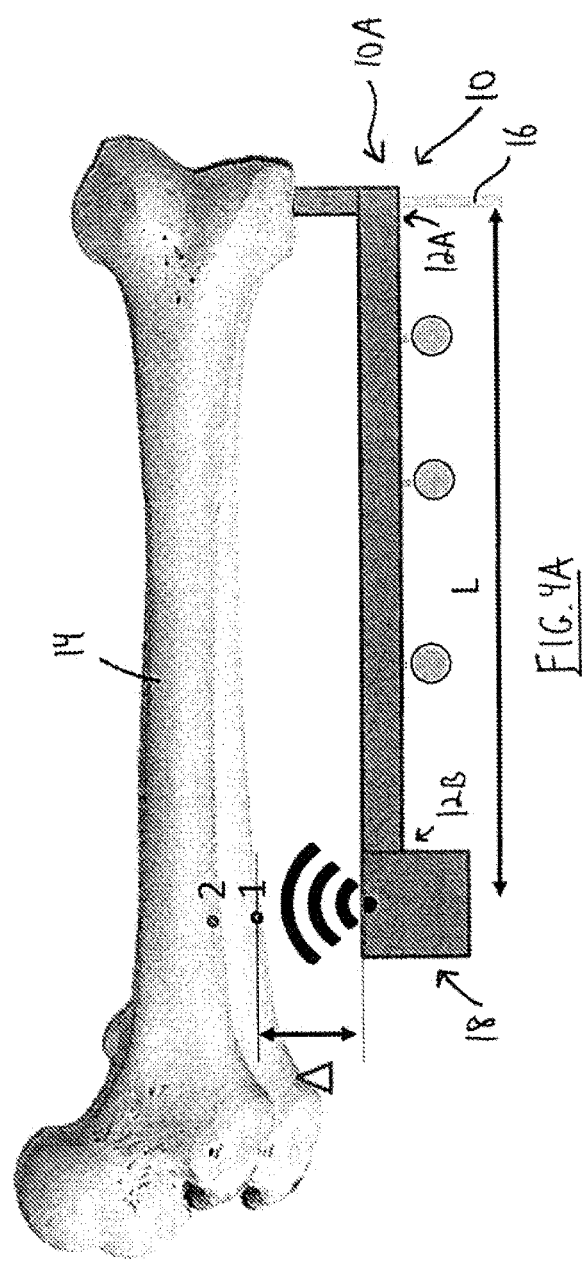
FIG. 4A
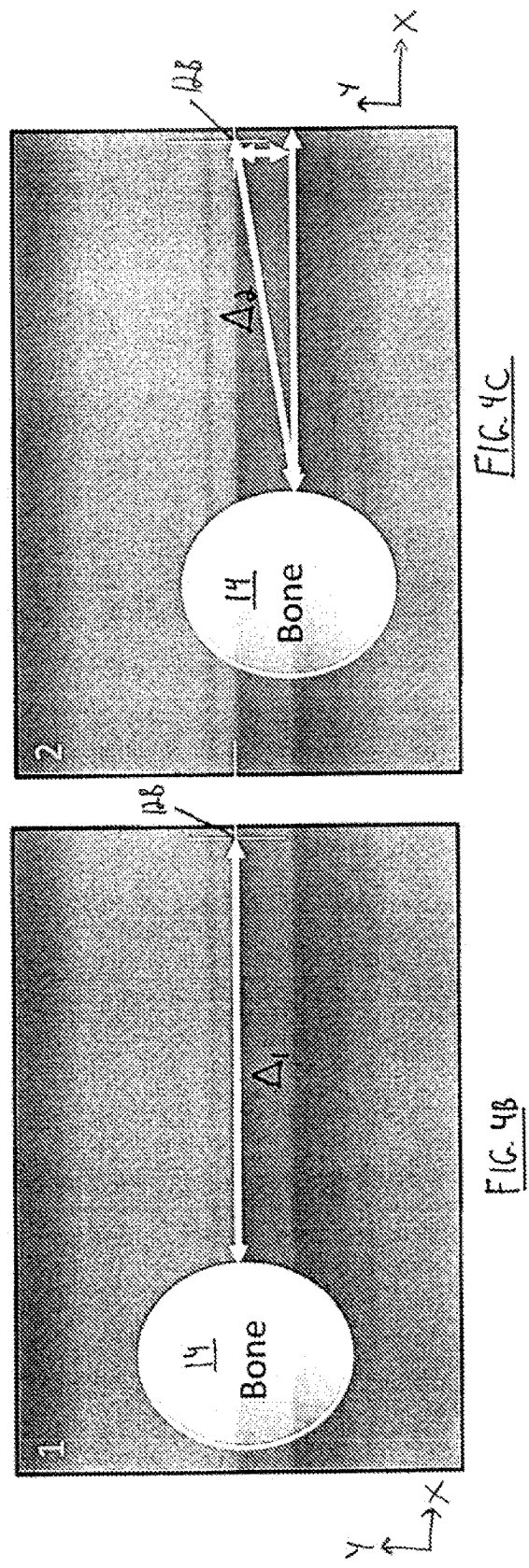
FIG. 4C
FIG. 4B

SYSTEM AND METHOD FOR TRACKING BONES

CROSS-REFERENCE TO RELATED APPLICATIONS

This application claims priority to U.S. provisional patent application 62/725,639 filed Aug. 31, 2018, the entire content of which is incorporated by reference herein.

TECHNICAL FIELD

The present disclosure relates to the field of computer-assisted medical procedures and, more specifically, to bone tracking and positioning in computer-assisted surgery (CAS) systems, also known as navigation in CAS systems.

BACKGROUND

Computer-assisted surgery (CAS) makes use of markers (a.k.a., trackers) fixed to the patient to track bones before and during surgery. Conventional trackable markers need to be anchored to the bone and often include surgical pins which are inserted into the bones to be tracked. These pins, inserted into the bones before or during the surgery, may be of different diameter sizes and are relatively invasive. The insertion of such pins adds an extra step to the surgery and does not contribute to treatment, their only purpose being to assist surgical tracking of the bone. The installation of such pins can also be time-consuming.

Furthermore, the length of the pins is sometimes obtrusive to the surgeon who may therefore cut them to a length better adapted to the surgeon's movement during the surgery. The need to sometimes cut the pins in this regard is also perceived as an additional step not particularly appreciated by surgeons, and the cut ends of pins may be sharp and hazardous to the personnel working around the surgery table.

An alternate option for tracking bones is to position such markers in a non-invasive manner, for instance on soft tissue. However, in such a scenario, care must be taken to avoid movement of the trackers relative to the bone, and this may entail limiting movements of the limb due to the soft tissue interfacing the trackers to the bone. Consequently, the surgeon's maneuvers may be hampered when securing markers to soft tissue.

SUMMARY

There is provided a system for determining a position and an orientation of a bone of an anatomical feature, the bone underlying an outer-skin surface of the anatomical feature, the system comprising: a trackable reference device having a surgical pin at a first position on the trackable reference device, the surgical pin being attachable to the bone to anchor the trackable reference device to the bone; a wearable attachment attached to the trackable reference device and configured to be mounted about the outer-skin surface of the anatomical feature to mount the trackable reference device to the outer-skin surface; at least one distance sensor mounted to the trackable reference device at a second position thereon and operable to determine a distance measurement of the second position of the trackable reference device from the bone; at least one reference marker array having a plurality of reference markers fixedly mounted to the trackable reference device; a fixed reference defining a reference coordinate system; a position sensing device operable to register position and orientation readings of the reference markers in the reference coordinate system; and a processing unit operable to receive the position and orientation readings from the position sensing device, and to receive the distance measurement of the second position of the trackable reference device from the bone, the processing unit being operable to determine the position and the orientation of the bone in the reference coordinate system using the position and orientation readings and the distance measurement.

There is provided a method of determining a position and an orientation of a subcutaneous bone of an anatomical feature, the method comprising: anchoring a portion of a trackable reference device to the bone; removably mounting a remainder of the trackable reference device to skin around the bone; determining a distance of a position of the trackable reference device from the bone; registering position and orientation readings of reference markers fixedly attached to the trackable reference device in a reference coordinate system; determining the position and the orientation of the bone in the reference coordinate system using the position and orientation readings and the distance of the position of the trackable reference device from the bone.

There is provided a wearable trackable reference device for determining a position and an orientation of a bone of an anatomical feature, the bone underlying an outer-skin surface of the anatomical feature, the wearable trackable reference device comprising: a surgical pin at a first position on a body of the trackable reference device, the surgical pin being attachable to the bone to anchor the body to the bone; a wearable attachment configured to be mounted about the outer-skin surface of the anatomical feature to mount the body to the outer-skin surface; at least one distance sensor at a second position on the body and operable to determine a distance measurement of the second position of the body from the bone; and at least one reference marker array having a plurality of reference markers fixedly mounted to the body.

BRIEF DESCRIPTION OF THE DRAWINGS

Reference is now made to the accompanying figures in which:

FIG. 4A is a perspective view of the trackable reference device of FIG. 1 for tracking a bone that has undergone movement between a first position and a second position;

FIG. 4B is a view of an image generated by the computer-assisted surgery system of FIG. 1 based on the first position of the bone; and FIG. 4C is a view of an image generated by the computer-assisted surgery system of FIG. 1 based on the second position of the bone.

DETAILED DESCRIPTION

Figure 1:
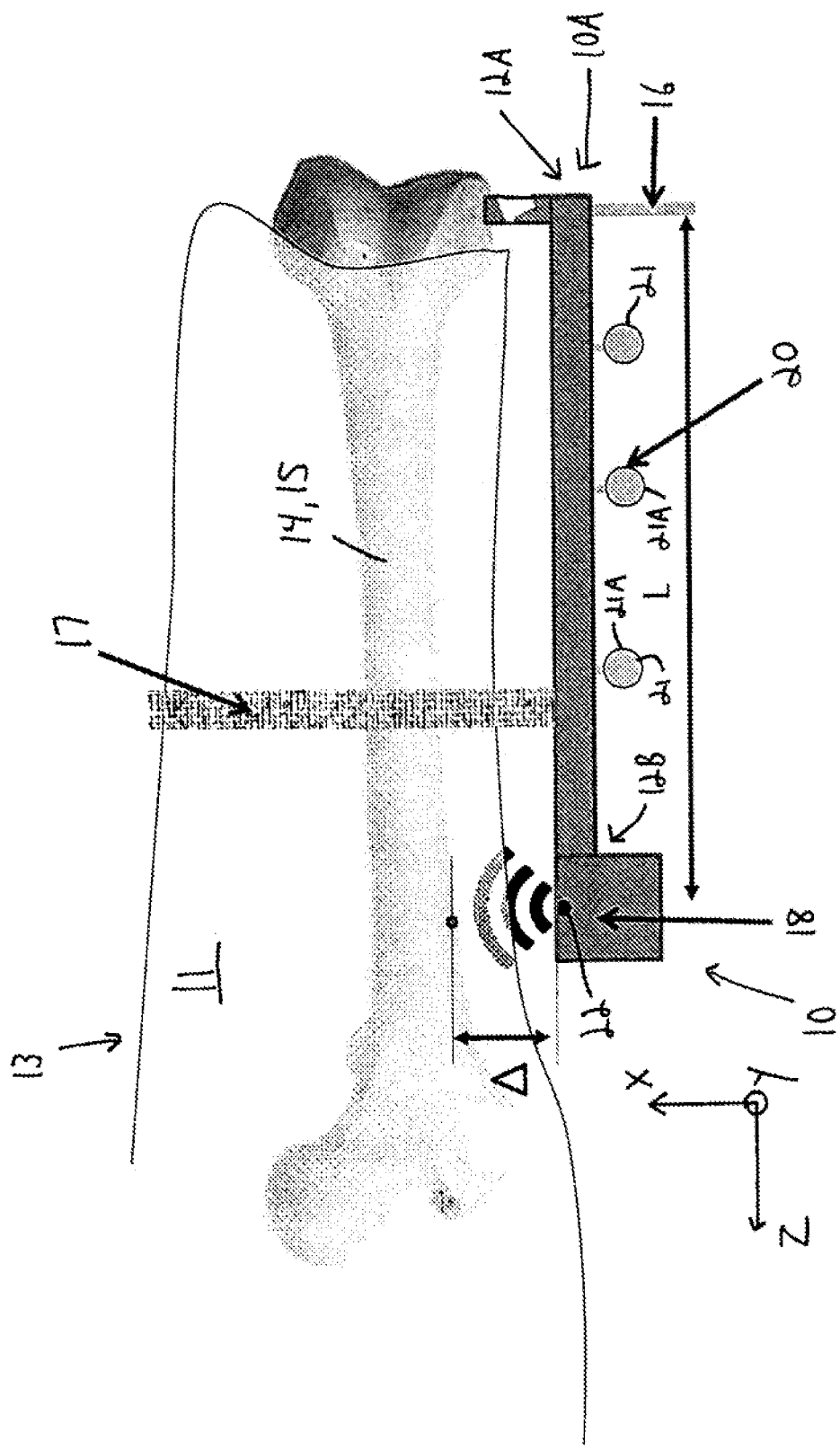
FIG. 1 is a perspective view of a trackable reference device being trackable in a computer-assisted surgery system.

FIG. 1 illustrates a wearable trackable reference device 10 (sometimes referred to herein simply as "device" 10) that is removably mounted about an outer-skin surface 11 (e.g., exposed skin, epidermis, external soft tissue, etc.) of an anatomical feature, such as but not limited to a leg portion 13 of a patient. The position and/or orientation of the device 10 can be tracked through space. The wearable device 10 and the system using it, as will be described herein, may also be used to determine the position and/or orientation of body parts other than the leg portion 13 of a patient, such as anatomical features of arms (elbows, wrists, hands, etc.), or of legs (e.g. femur, tibia, fibula, pelvis, etc.), and the like. The leg portion 13 includes a bone 14, which is a femur 15 in the depicted embodiment. The bone is largely subcutaneous, in that a majority thereof is disposed beneath, and thus substantially underlies, the outer-skin surface 11 of the anatomical feature in question. In certain embodiments, the bone 14 may thus be said to be substantially unexposed. However, it is to be understood that one or more portions of the bone 14 may be exposed during surgery, for example as a result of one or more incision(s) made as part of the surgical technique being employed. Accordingly, while portions of the bone 14 may be exposed during surgery with the anatomical feature within the device 10, the bone 14 will otherwise remain substantially subcutaneous, if not completely subcutaneous. While the bone 14 may be described herein as "underlying" the outer-skin surface 11 it is to be understood that this does not exclude the possibility that certain portions of the bone 14 may be at least partially exposed during surgery (e.g. by incisions, etc.) nor does this require or imply that the entirety of the bone 14 must necessarily be unexposed and subcutaneous at all times.

The device 10 is configured to be mounted about the anatomical feature. This mounting may take different configurations. In the depicted embodiment, the device 10 is loosely mounted about the outer-skin surface 11 of the anatomical feature such that it can displace with respect to the outer-skin surface 11. In an alternate embodiment, the device 10 is mounted to the anatomical feature in such a way that there is negligible or no movement between the device 10 and the anatomical feature. The position and/or orientation of the device 10 are also trackable through space, whereby a tracking of the anatomical feature and the bone 14 can be derived from a tracking of the device 10. The device 10 is therefore a tool to be used to track the position and the orientation, and thus the movement, of the bone 14 through space. It is therefore appreciated that the device 10 can take different forms to accomplish such functionality.

The device 10 is in the form of a rod 10A in the depicted embodiment. Other shapes and configurations for the device 10 are possible and within the scope of the present disclosure, such as a strip, a block, a plate, etc. The device 10 is mountable about other limbs, appendages, or other anatomical features of the patient having a bone 14 to be tracked. Still referring to FIG. 1, the device 10 is mounted about the leg portion 13 and some portion of the device 10 is attached or fixed to the bone 14. In the depicted embodiment, the rod 10A extends between a first end 12A and a second end 12B opposite the first end 12A. The rod 10A has a surgical pin 16 at a first position on the rod 10A, which is at or near the first end 12A in the depicted embodiment. When the rod 10A is being used, the surgical pin 16 is attached by the surgeon to the bone 14 to anchor the rod 10A to the bone 14. In FIG. 1, the second end 12B is not attached to the bone 14, and is thus free to move relative thereto. The surgical pin 16 may be attached to the bone 14 through the outer-skin surface 11, or may also be attached to an exposed portion of the bone 14. The surgical pin 16 may be any one of a nail, screw, or other mechanical fastener. In an embodiment, the surgical pin 16 is a polyaxial screw permitting pivoting motion of the rod 10 in multiple dimensions, and reference is made in this regard to US 2005/0203528 A1 to common assignee Orthosofit Inc., the entire contents of which are incorporated by reference herein.

A remainder of the rod 10A shown in FIG. 1 is mounted about the outer-skin surface 11 of the leg portion 13 with a wearable attachment 17. In an alternate embodiment, the device 10 is free of the wearable attachment 17. In FIG. 1, the wearable attachment 17 is attached to the rod 10A and configured to be mounted about the outer-skin surface 11 of the leg portion 13. The mounting of the wearable attachment 17 attaches the device 10 to the leg portion 13. In the depicted embodiment, mounting the wearable attachment 17 to the leg portion 13 to thereby mount the rod 10A also helps to position the rod 10A in approximate alignment with the femur 15 of the leg portion. For example, mounting the wearable attachment 17 to the leg portion 13 to thereby mount the rod 10A may help to orient the rod 10A parallel to an axis of the femur 15. The wearable attachment 17 is mounted to the rod 10A in the depicted embodiment between the first and second ends 12A,12B, for instance with the wearable attachment being closer to the second end 12B. The wearable attachment 17 is a band in the depicted embodiment. Other shapes and configurations for the wearable attachment 17 are possible and within the scope of the present disclosure. In an alternate embodiment, the wearable attachment 17 is a strap. In another alternate embodiment, the wearable attachment 17 is a U-shaped holder. In yet another alternate embodiment, the wearable attachment 17 is a sleeve.

Still referring to FIG. 1, one or more distance sensors 18 are removably mounted to the device 10 at a second position. The second position in the depicted embodiment is the second end 12B of the rod 10A, though it may be at other locations as well. The second position is thus spaced apart from the first position a known distance L. In FIG. 1, the distance sensor 18 is immobile on the rod 10. In FIG. 1, the distance sensor 18 does not move relative to the rod 10A or relative to the surgical pin 16 when mounted to the rod 10A. The distance sensor 18 is operable to determine a distance measurement or distance $\Delta$ of the second position of the device 10 (e.g. the second end 12B of the rod 10A) from the bone 14. In an alternate embodiment, one or more of the distance sensors 18 moves in a known manner relative to the device 10 so that its position on the device 10 can be determined.

In the embodiment of FIG. 1, the distance sensor 18 is active. Stated differently, each distance sensor 18 is operable to emit an electromagnetic wave, to receive an echo of the wave off of a surface of the bone 14, and to record a time measurement for the echo. This enables the calculation of the distance $\Delta$ of the bone 14 from the distance sensor 18, and thus from the device 10. The distance $\Delta$ may be a vector, which includes components in one or more of the axes X, Y (shown into and out of the page in FIG. 1) and Z. In the depicted embodiment where the bone 14 is the femur 15, the vector for the distance $\Delta$ will have components in the X and Y axes, because the position of the distance sensor 18 on the rod 10A in the Z axis is fixed.

For joints with two bones (e.g. the knee, having the femur and tibia), the rods 10A may be mounted on each bone such that the distance sensors 18 of each are in proximity to each other at the joint (e.g. the knee). The two distance sensors 18 may measure the distance between each other at a given moment. The distance sensors 18 may also contain inertial navigation sensors (e.g. IMUs) capable of tracking the orientation of each distance sensor 18. With the known distance between the two distance sensors 18 and a relative orientation, the values for flexion/extension and varus/valgus of the knee joint can be outputted in real time to the operator/surgeon.

In the illustrated embodiment, one or more of the distance sensors 18 includes an ultrasound device 22. The ultrasound device 22 is a transducer that emits an ultrasound wave and measures the time it takes for the wave to echo off of a hard surface (such as the bone 14) and to return to the transducer face. Using the known speed of the ultrasound wave, the time measurement is translated into the distance $\Delta$ between the distance sensor 18 and the bone 14 located below the surface of the outer-skin surface 11. As will be explained below, knowing the distance $\Delta$ allows for the bone 14 to be tracked through space.

In an alternate embodiment, the distance sensor 18 is passive and employs passive techniques to identify the bone landmarks. In one such embodiment where the device 10 is in the form of the rod 10A, the passive distance sensor 18 is positioned on the rod 10A in locations that are known to substantially overlie landmarks of the bone 14. Each passive distance sensor 18 may include a reflector. The distance $\Delta$ between the distance sensor 18 and the landmarks of the bone 14 can then be suitably approximated.

Still referring to FIG. 1, one or more reference marker arrays 20 are fixedly mounted to the device 10. Each reference marker array 20 helps to track the position and the orientation of the device 10 through space, and thus helps to track the position and the orientation of the bone 14 through space. Each reference marker array 20 is in fixed relationship with the device 10 such that the geometric relationship of each reference marker array 20 with the device 10, and with any other reference marker arrays 20, is known. The position and the orientation of the reference marker arrays 20 with respect to the bone 14 will also remain substantially constant because the device 10 is anchored to the bone 14 with the surgical pin 16.

In the depicted embodiment, each reference marker array 20 is mounted to a portion of the rod 10A which is stationary, and thus does not undergo displacement relative to the structure of the rod 10A. In an alternate embodiment, one or more of the reference marker arrays 20 are mounted to a portion of the rod 10A which undergoes displacement. Therefore, the reference marker arrays 20 undergo displacement in a known manner. Their geometric relationship therefore varies in a known fashion with the displacement of the rod 10A, and thus the relative movement between the reference marker arrays 20 can be compensated for.

Each reference marker array 20 has multiple reference markers 21. The term "reference marker" is intended to mean an active or passive marker, such as an emitter or a reflector. Each reference marker 21 is therefore an active or passive trackable object, and can operate using optical, RF, ultrasound, or electromagnetic signals. In FIG. 1, each reference marker 21 is fixedly mounted to the device 10. In the depicted embodiment, the reference markers 21 are fixedly mounted to the rod 10A between the first and second ends 12A,12B. In an alternate embodiment, the reference markers 21 are mounted elsewhere on the rod 10A. The reference markers 21 do not undergo displacement relative to the device 10 and to one another, and thus their geometric relationship remains substantially constant even as the rod 10A undergoes movement.

In FIG. 1, each reference marker array 20 includes three reference markers 21. The reference markers 21 protrude from the surface of the rod 10A away therefrom. The reference markers 21 in the depicted embodiment are optical trackers 21A, and function as retro-reflective references for tracking the device 10 and anatomical feature in six DOFs, by a component of the computer-assisted surgery system, as described in greater detail below. In an embodiment, the retroreflective reference markers 21 are in a known pattern, the reference markers 21 being optically tracked by the recognition of the known pattern by a camera. As an alternative to optical tracking, the reference markers 21 may include inertial sensors (e.g., accelerometers, gyroscopes, etc) that produce tracking data to be used to continuously update the position and/or orientation of the device 10. Other types of tracking technology may also be used.

Figure 2:
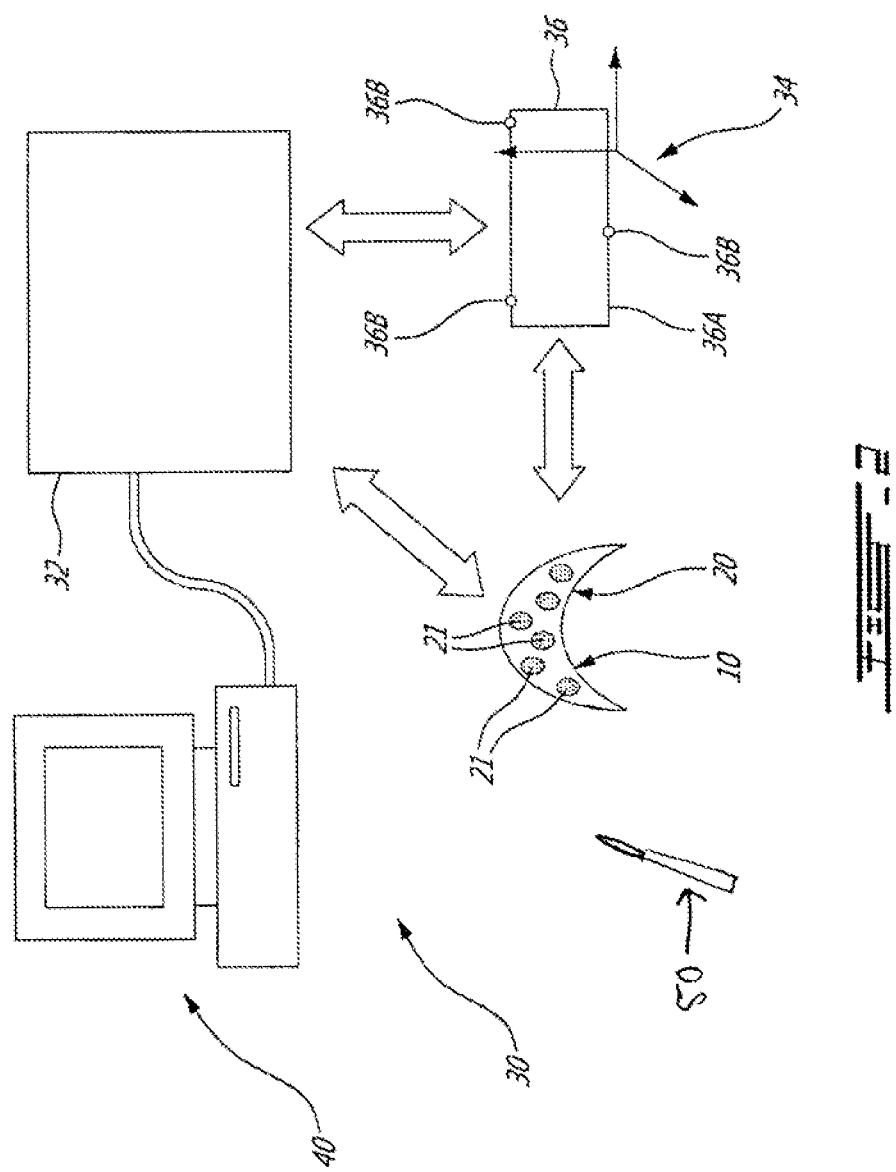
FIG. 2 shows a system for determining a position and an orientation of bone, which underlies an outer-skin surface, in space.

Referring to FIG. 2, there is also disclosed a system 30 for determining a position and an orientation of the bone 14 in space. The system 30 is a computer-assisted surgery (CAS) system. The system 30 includes one or more wearable devices 10. In the illustrated embodiment, the device 10 is shown with its reference marker array 20. It will be noted that throughout the figures, like features are identified by like reference numerals.

The system 30 also includes a position sensing device 32. The position sensing device 32 is used with the CAS system 30 to continuously track the position and/or orientation in space of the reference markers 21, and thus, of the bone 14, as explained in greater detail below. The position and orientation of the reference markers 21 may be tracked in a reference coordinate system 34, namely a virtual x,y,z set of axes that is used to quantify movements of the bone 14 and the device 10 relative to tools 50 used to perform surgery on the bone 14 (e.g. drill, saw, cut guide, etc). In FIG. 2, the reference coordinate system 34 is defined by a fixed reference 36 that is separate from the device 10. In another embodiment, the reference coordinate system 34 is fixed to the bone 14. Many different configurations of the position sensing device 32 which accomplish the above-described functionality are possible and within the scope of present disclosure. For example, and as shown in the illustrated embodiment, the position sensing device 32 is a distinct component which communicates with and/or optically tracks the reference markers 21 and with the fixed reference 36. In another embodiment, the position sensing device 32 is part of the fixed reference 36.

According to an embodiment, the position sensing device 32 helps to track the device 10 and reference marker arrays 20 on the device 10 and on tools 50, without the assistance of any fixed reference 36. However, the system 30 may also operate with the fixed reference 36. The fixed reference 36 has a known and a fixed position within the reference coordinate system 34 and is used to position and orient the device 10, and thus the bone 14, in space within the reference coordinate system 34. The fixed reference 36 is therefore any active or passive device, with a known position in the reference coordinate system 34. In the illustrated embodiment of FIG. 2, the fixed reference 36 is the OR surgery table 36A which remains fixed in position within the reference coordinate system 34. A plurality of trackers 36B are fixedly mounted to the surgery table 36A. The trackers 36B are spaced apart from one another, and are calibrated before the surgery to define the reference coordinate system 34. According to an embodiment, the plane of the OR surgery table 36A, represented by the trackers 36B, is assumed to be and entered in the reference coordinate system 34 as being a frontal or sagittal plane of the patient lying in supine decubitus or lateral decubitus. The trackers 36B also communicate with the reference markers 21 on the device 10 to track their position and orientation through space.

In the embodiment of FIG. 2, the trackers 36B are ultrasound trackers, and are fixed in position and spaced apart from each other to define the reference coordinate system 34. The ultrasound trackers 36B form part of the position sensing device 32 in an embodiment featuring the fixed reference 36. They are operable to emit ultrasound waves and measure the time it takes for the wave to echo off of a corresponding reference marker 21 and to return to the ultrasound tracker 36B. Using the known speed of the ultrasound wave, the time measurement is translated into a distance value between the corresponding reference marker 21 and the ultrasound tracker 36B. This distance value can then be used to determine the position and orientation coordinates of the reference marker 21 within the reference coordinate system 34. Since the geometric relationship between the reference marker 21 and the device 10 is known, the distance value can also be used to determine the position and orientation coordinates of the device 10 within the reference coordinate system 34. Furthermore, since the device 10 is anchored to the bone 14 with the surgical pin 16, and since the distance Δ of the device 10 from the bone 14 is known from the distance sensor 18, the distance value can also be used to determine the position and orientation coordinates of the bone 14 within the reference coordinate system 34. In alternate embodiments, the trackers 36B of the fixed reference 36 emit other electromagnetic signals (e.g. RF), or emit optical signals.

In the illustrated embodiment of FIG. 2, the trackers 36B communicate with the reference markers 21 on the device 10 to generate position and orientation readings by triangulation. At least two reference trackers 36B are fixed in position within the reference coordinate system 34. These at least two trackers 36B form two or more known points in the reference coordinate system 34, and a baseline length is determined between them. A third point in the reference coordinate system 34, such as the position of one of the reference markers 21, can then be determined with respect to the two points formed by the trackers 36B. Therefore, the position and/or orientation of the reference marker 21 can be determined within the reference coordinate system 34. The trackers 36B therefore help to locate the bone 14, by triangulating the position of one or more reference markers 21 fixed on the device 10 with respect to at least two reference trackers 36B in a known location in the reference coordinate system 34.

Still referring to FIG. 2, the CAS system 30 also has a processing unit 40. The processing unit 40 is in communication with the position sensing device 32 to process the position and orientation readings of the reference markers 21 at a given time interval. The processing unit 40 measures or tracks time intervals. In some embodiments, the processing unit 40 is a part of the position sensing device 32. The processing unit 40 therefore includes any number of suitable components for performing the above functionality, such as an internal central processing unit (CPU), a memory unit, and a storage unit. The processing unit 40 can be any of a number of computing devices running a variety of applicable operating systems. The processing unit 40 may also include a display device, such as a monitor. The processing unit 40 may also include one or more input devices such as keyboards, pointing devices, and the like. The processing unit 40 runs various modules, in the form of algorithms, code, non-transient executable instructions, etc., in order to operate the CAS system 30 in the manner described herein.

Figure 3:
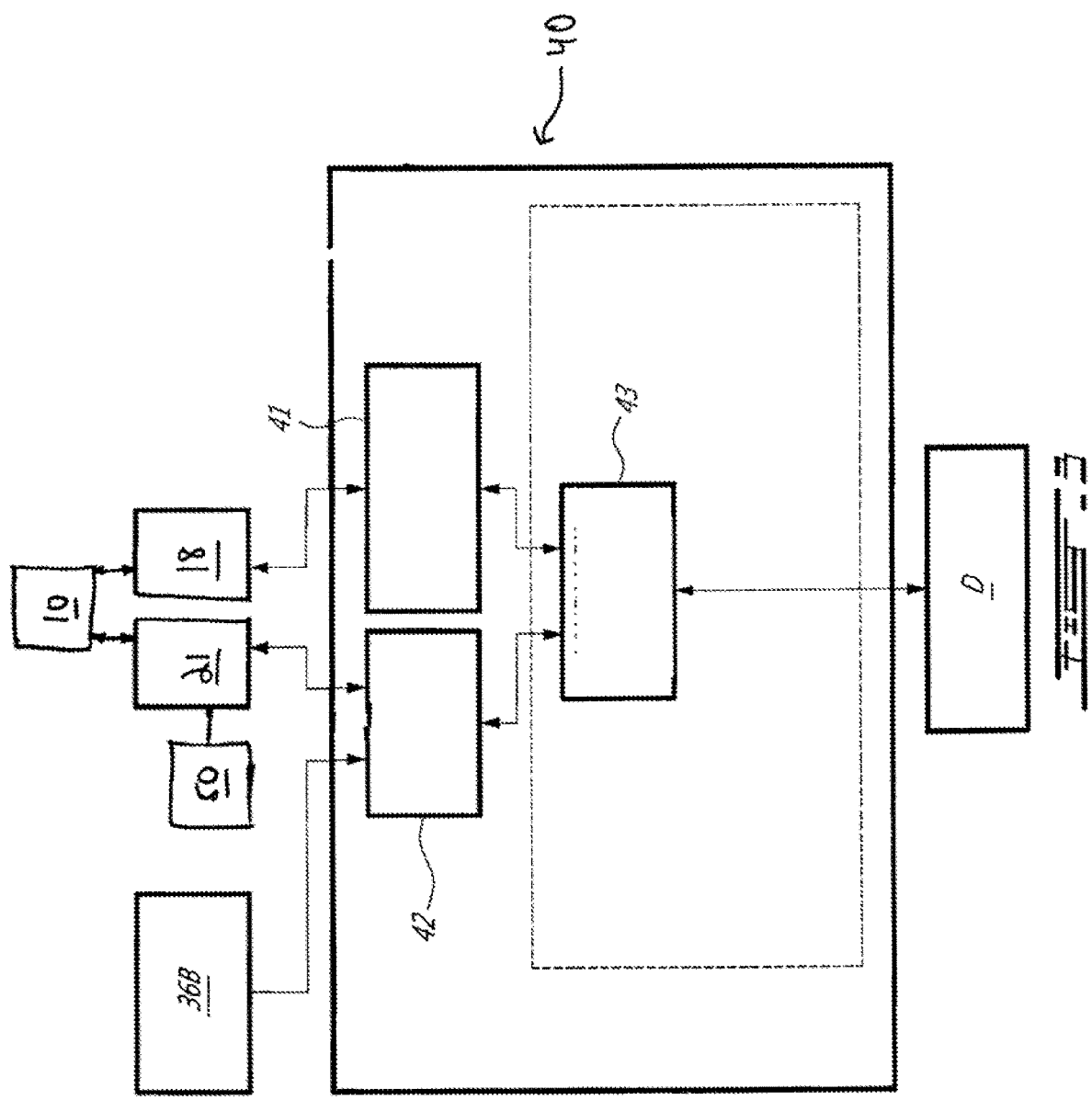
FIG. 3 is a block diagram of a processing unit of the system of FIG. 2.

Referring to FIG. 3, the processing unit 40 includes, or communicates with, one or more interfaces D, for the information to be provided to the operator (e.g. the surgeon). The interfaces D may be monitors and/or screens including wireless portable devices (e.g., phones, tablets), audio guidance, LED displays, among many other possibilities. For example, the interface D comprises a graphic user interface (GUI) operated by the CAS system 30. The interface D may also display images outputted by the processing unit 40, for instance to track the bone 14 through space.

The processing unit 40 has a bone distance module 41. In operation, the bone distance module 41 receives data from the distance sensor 18 and processes the data to determine the distance of the device 10 from the bone 14. This may be done continuously during navigation to monitor any movement between the device 10 and the bone 14, if any. In an embodiment, the bone distance module 41 commands the distance sensor 18 or components thereof (e.g. ultrasound devices) to emit waves (electromagnetic, ultrasound) and then measures the time it takes for the wave to echo off of the bone 14 and to return to the distance sensor 18. Using the known speed of the wave, the bone distance module 41 translates the time measurement into the distance Δ between the distance sensor 18 and the bone 14 located below the surface of the outer-skin surface 11.

The processing unit 40 also has a device tracking module 42. The device tracking module 42 is configured to output position and orientation readings of the reference markers 21 or like markers on the device 10 in the reference coordinate system 34. The position and orientation readings help to determine the position and orientation of the bone 14 in the reference coordinate system 34, and thus help to track the bone 14 in space. If the fixed reference 36 is present, the device tracking module 42 receives active feedback from the trackers 36B to determine the position of the reference markers 21 within the reference coordinate system 34. The device tracking module 42 is operable to process data using any one of the different techniques for tracking the reference markers 21 or like markers described above. For example, the device tracking module 42 can triangulate the position and orientation readings of the reference markers 21 with the two or more reference trackers 36B fixed in position within the reference coordinate system 34. More particularly, the device tracking module 42 calculates the baseline length between the trackers 36B in the reference coordinate system 34. The device tracking module 42 then determines the position and orientation of a third point in the reference coordinate system 34 (i.e. one of the reference markers 21) using triangulation with respect to the two points formed by the trackers 36B.

The processing unit 40 also has tracking module 43. The tracking module 43 in operation receives the position and orientation readings of the reference markers 21 from the device tracking module 42. The tracking module 43 in operation also receives the distance Δ information from the bone distance module 41. With this information, the tracking module 43 is able to generate data on the position and orientation of the bone 14 in order to track the position and/or orientation of the bone 14 within the reference coordinate system 34. The position and orientation readings of the reference markers 21 allow the tracking module 43 to determine the position and orientation of the device 10 in the reference coordinate system 34 because the geometric relationship between the reference markers 21 and the device 10 is known. Since the position and orientation of the device 10 within the reference coordinate system 34 is known, the tracking module 43 is operable to determine the position and/or orientation of the bone 14 in the reference coordinate system 34 because the geometric relationship between the bone 14 and the device 10 is known with the distance Δ provided by the distance sensor 18. Therefore, the tracking module 43 is operable to track the bone 14 through space within the reference coordinate system 34. The tracking module 43 outputs position and orientation readings of the bone 14 to the interface D.

It will therefore be appreciated that the CAS system 30 allows the position and/or orientation of a bone 14 to be tracked in a reference coordinate system 34 by simply tracking the movement of a device 10 mounted about the outer-skin surface 11 of the anatomical feature containing the bone 14. The position and orientation of the device 10 is therefore actively tracked in the CAS system 30, and from the position and orientation readings of the device 10, the CAS system 30 indirectly determines the position and/or orientation of the bone 14 underlying the device 10 and in geometric relationship therewith. In at least some of the embodiments described above, the CAS system 30 determines the position and/or orientation of the bone 14 without having to continuously image the bone 14 itself, which can reduce system processing times.

The device 10 disclosed herein uses only one surgical pin 16 to anchor the device 10 to the bone 14. In so doing, the device 10 helps to reduce the number of surgical pins 16 used in bone tracking, and the complications and inconveniences associated with too many surgical pins 16. By having one single fixation with the surgical pins 16 and the distance sensor 18, the device 10 is able to track the movement of the bone 14 around a single attachment point on the bone 14. If relative movement occurs between the device 10 and the bone 14, the readings from the distance sensor 18 will be used to correct the position and/or orientation of the bone 14 in the coordinate system. In an embodiment, the single attachment point is a hinge or a ball joint, which allows the distance sensor 18 to rotate or pivot in, for example, about the X axis shown in FIG. 1.

Referring to FIGS. 4A to 4C, the bone 14 may move relative to the device 10 between sequential time intervals because the rod 10A in the depicted embodiment is anchored to the bone 14 at only the first end 12A with the surgical pin 16. In some embodiments, the wearable attachment 17 may be mounted tightly enough to render the device 10 immobile on the outer-skin surface 11. However, in other cases, while it may reduce significant movements of the device 10 relative to the bone 14, the wearable attachment 17 may not be mounted tightly enough to render the device 10 immobile on the outer-skin surface 11. The CAS system 30 is therefore operable to determine if the bone 14 has moved relative to the device 10 between two time intervals, and to compensate for that movement when tracking the position and orientation of the bone 14, via the added information provided by the distance sensor 18 complementing the tracking done by the position sensing device 32 using the arrays 20.

In FIG. 4A, the bone 14 moves relative to the device 10 from position 1 to position 2 during a surgical intervention, for example. The distance sensor 18 is able to determine that the distance Δ separating the second end 12B of the rod 10A from the bone 14 has changed between position 1 and 2, and will output the distance Δ at both position 1 and position 2 to the bone distance module 41. The bone distance module 41 will output to the tracking module 43 the difference in the distance Δ value measured for position 1 and position 2 at two sequential time intervals. This difference value alerts or signals to the processing unit 40 that the bone 14 has moved relative to the device 10. The tracking module 43 will then update the data on the position and orientation of the bone 14 to compensate for the new position of the bone 14 with respect to the device 10, in order to track the position and/or orientation of the bone 14 within the reference coordinate system 34.

For example, FIG. 4B shows the distance $\Delta_1$ between the bone 14 and the second end 12B of the rod 10A at position 1, and FIG. 4C shows the distance $\Delta_2$ between the bone 14 and the second end 12B of the rod 10A at position 2. The distance $\Delta_1$ at position 1 has a component in only the X axis, and no component in the Y axis. The distance $\Delta_2$ at position 2 has a component in the X axis, and a component in the Y axis, showing that the bone 14 has moved relative to the device 10 in the X and Y direction. The different distance $\Delta_2$ at position 2 outputted by the bone distance module 41 to the tracking module 43 allows the tracking module 43 to compare the distances $\Delta_1$ and $\Delta_2$, and to use the different distances to adjust the position and/or orientation of the bone 14 in the reference coordinate system 34. In the embodiment where the surgical pin 16 is polyaxial or a ball/socket joint, a mechanical (e.g. rotary) or optical encoder may be used to measure rotation of the rod 10A, and therefore measure displacement in the Z axis. With a known Z axis displacement, the X and Y components of the distance change may also be determined. Thus, the position and orientation of the bone 14 may be adjusted in the reference coordinate system 34.

The above description is meant to be exemplary only, and one skilled in the art will recognize that changes may be made to the embodiments described without departing from the scope of the invention disclosed. Still other modifications which fall within the scope of the present invention will be apparent to those skilled in the art, in light of a review of this disclosure, and such modifications are intended to fall within the appended claims.

The invention claimed is:

1. A system for determining a position and an orientation of a bone of an anatomical feature, the bone underlying an outer-skin surface of the anatomical feature, the system comprising:

a trackable reference device having an elongated body extending linearly between a first end and a second end, the first end and the second end being axially spaced part along a longitudinal axis defined by the elongated body of the trackable reference device, a surgical pin mounted to the trackable reference device at the first end thereof to anchor the trackable reference device to the bone at the first end, the first end defining a first position along the longitudinal axis of the trackable reference device;

at least one distance sensor fixedly mounted to the trackable reference device at a second position on the trackable reference, the at least one distance sensor at the second position being axially spaced apart a fixed distance along the longitudinal axis from the surgical pin at the first position, the at least one distance sensor operable to determine a distance measurement between the trackable reference device and the bone, at the second position, in a transverse direction relative to the longitudinal axis;

a wearable attachment attached to the trackable reference device at an axial position located between the first position and the second position along the longitudinal axis, the wearable attachment configured to be mounted about the outer-skin surface of the anatomical feature to mount the trackable reference device to the outer-skin surface;

at least one reference marker array having a plurality of reference markers mounted to the trackable reference device at respective fixed positions along the elongated body of the trackable reference device between the surgical pin and the at least one distance sensor;

a fixed reference defining a reference coordinate system;

a position sensing device operable to register position and orientation readings of the reference markers in the reference coordinate system; and a processing unit operable to receive the position and orientation readings from the position sensing device, and to receive the distance measurement of the second position of the trackable reference device from the bone, the processing unit being operable to determine the position and the orientation of the bone in the reference coordinate system using the position and orientation readings and the distance measurement.

2. The system of claim 1, wherein the at least one distance sensor is fixedly mounted to the trackable reference device at the second end.

3. The system of claim 1, wherein the at least one distance sensor is operable to actively emit an electromagnetic wave, and to receive an echo of the electromagnetic wave off of a surface of the bone.

4. The system of claim 1, wherein the at least one distance sensor includes an ultrasound device.

5. The system of claim 1, wherein the wearable attachment is configured to mount the trackable reference device to the anatomical feature with the longitudinal axis of the elongated body of the trackable reference device parallel to a longitudinal axis of the bone.

6. The system of claim 1, wherein the wearable attachment is attached to the trackable reference closer to the second end than to the first end.

7. The system of claim 1, wherein the wearable attachment is one of a band, a strap, a U-shaped holder, and a sleeve.

8. The system of claim 1, wherein the trackable reference device is pivotable about an axis defined by the surgical pin upon the surgical pin being attached to the bone.

9. A method of determining a position and an orientation of a subcutaneous bone of an anatomical feature, the method comprising:

anchoring a portion of a trackable reference device to the bone using a surgical pin to fasten a single end of the trackable reference device to the bone, the single end defining a first portion on the trackable reference device;

removably mounting a remainder of the trackable reference device to skin around the bone using a wearable attachment located at a second position of the trackable reference device spaced axially apart from the first position along a longitudinal axis of the trackable reference;

determining a distance between the trackable reference device and the bone at a third position along the longitudinal axis of the trackable reference, the second position disposed axially between the first position and the third position along the longitudinal axis;

registering position and orientation readings of reference markers fixedly attached to the trackable reference device in a reference coordinate system;

determining the position and the orientation of the bone in the reference coordinate system using the position and orientation readings and the distance of the position of the trackable reference device from the bone.

10. The method of claim 9, wherein determining the position and the orientation of the bone in the reference coordinate system includes indirectly determining the position and the orientation of the bone in the reference coordinate system by determining the position and the orientation of the trackable reference device in the reference coordinate system.

11. The method of claim 9, wherein determining the position and the orientation of the bone in the reference coordinate system includes triangulating position and orientation of the reference markers in the reference coordinate system, and using the distance of the position of the trackable reference device from the bone.

12. The method of claim 9, wherein determining the distance of the position of the trackable reference device from the bone includes emitting an electromagnetic wave, and receiving an echo of the electromagnetic wave off of a surface of the bone.

13. The method of claim 9, wherein determining the distance of the position of the trackable reference device from the bone includes emitting an ultrasonic wave.

14. The method of claim 9, wherein determining the distance of the position of the trackable reference device from the bone includes signaling that the trackable reference device has moved relative to the bone when a first distance of the position of the trackable reference device from the bone at a first time interval is different from a second distance of the position of the trackable reference device from the bone at a second sequential time interval.

15. The method of claim 14, wherein determining the position and the orientation of the bone in the reference coordinate system includes compensating for movement of the trackable reference device relative to the bone by using the second distance of the position of the trackable reference device from the bone.

16. The method of claim 9, wherein removably mounting the remainder of the trackable reference device includes mounting the trackable reference device to be substantially free of movement relative to bone.

17. The method of claim 9, wherein removably mounting the remainder of the trackable reference device includes mounting the trackable reference device to have an orientation parallel to a longitudinal axis of the bone.

18. The method of claim 9, wherein anchoring the portion of the trackable reference device to the bone includes anchoring the portion of the trackable reference device to the bone to form a pivot at the bone.

19. The method of claim 9, wherein registering the position and orientation readings of the reference markers includes defining the reference coordinate system with a fixed reference that is separate from the trackable reference device.

20. A wearable trackable reference device for determining a position and an orientation of a bone of an anatomical feature, the bone underlying an outer-skin surface of the anatomical feature, the wearable trackable reference device comprising:

a surgical pin at a first position on a body of the trackable reference device, the first position defined along a longitudinal axis of the trackable reference device, the surgical pin being attachable to the bone to anchor the body to the bone;

a wearable attachment configured to be mounted about the outer-skin surface of the anatomical feature to mount the body to the outer-skin surface, the wearable attachment being axially spaced apart from the surgical pin and located at a second position along the longitudinal axis;

at least one distance sensor located at a third position on the body, the at least one distance sensor being axially spaced apart from the first position and the second position along the longitudinal axis, the at least one distance sensor operable to determine a distance measurement between the body of the wearable trackable reference the bone, at the third position, in a transverse direction relative to the longitudinal axis; and at least one reference marker array having a plurality of reference markers fixedly mounted at fixed positions along the body, between the surgical pin and the at least one distance sensor.

* * * * *